(12) United States Patent
Qi et al.

(10) Patent No.: US 9,967,555 B2
(45) Date of Patent: May 8, 2018

(54) SIMULATION DEVICE

(71) Applicant: HOYA CORPORATION, Tokyo (JP)

(72) Inventors: Hua Qi, Tokyo (JP); Hidetoshi Nishimura, Tokyo (JP)

(73) Assignee: HOYA CORPORATION, Tokyo (JP)

( * ) Notice: Subject to any disclaimer, the term of this patent is extended or adjusted under 35 U.S.C. 154(b) by 309 days.

(21) Appl. No.: 14/403,701

(22) PCT Filed: Apr. 23, 2013

(86) PCT No.: PCT/JP2013/061897
§ 371 (c)(1),
(2) Date: Nov. 25, 2014

(87) PCT Pub. No.: WO2013/175923
PCT Pub. Date: Nov. 28, 2013

(65) Prior Publication Data
US 2015/0163480 A1    Jun. 11, 2015

(30) Foreign Application Priority Data

May 25, 2012  (JP) .................................. 2012-119885

(51) Int. Cl.
*H04N 13/04* (2006.01)
*G02C 13/00* (2006.01)
(Continued)

(52) U.S. Cl.
CPC ......... *H04N 13/044* (2013.01); *A61B 3/0041* (2013.01); *A61B 3/032* (2013.01); *G02C 13/00* (2013.01)

(58) Field of Classification Search
CPC ...... A61B 3/0041; A61B 3/032; G02C 13/00; H04N 13/044
See application file for complete search history.

(56) References Cited

U.S. PATENT DOCUMENTS 6,329,989 B1    12/2001  Qi et al.
2006/0028400 A1*  2/2006  Lapstun ................. G02B 26/06
                                                                                345/8
(Continued)

FOREIGN PATENT DOCUMENTS

EP    2 105 088 A1    9/2009
EP    2 198 769 A1    6/2010
(Continued)

OTHER PUBLICATIONS

May 21, 2013 International Search Report issued in International Patent Application No. PCT/JP2013/061897.
(Continued)

*Primary Examiner* — Neil Mikeska
(74) *Attorney, Agent, or Firm* — Oliff PLC

(57) ABSTRACT

There is provided a simulation device for virtually displaying an image to be viewed through a spectacle lens by a wearer of a spectacle lens, including: an imaging camera configured to perform imaging in a visual field of the wearer; a depth sensor configured to acquire a depth image in the same view angle as an imaging result obtained by the imaging camera; a data acquisition unit configured to acquire lens data of the spectacle lens; an image creation unit configured to create a simulation image on which a view of an image to be viewed through the spectacle lens is reflected, by applying image processing to the imaging result obtained by the imaging camera, based on the depth image and the lens data; and an image displayer configured to display and output the simulation image as an image to be viewed through the spectacle lens.

7 Claims, 5 Drawing Sheets

(51) Int. Cl.
*A61B 3/00* (2006.01)
*A61B 3/032* (2006.01)

(56) References Cited

U.S. PATENT DOCUMENTS

| | | | |
|---|---|---|---|
| 2009/0248377 A1 | 10/2009 | Shinohara et al. | |
| 2010/0114540 A1 | 5/2010 | Shinohara et al. | |
| 2011/0075257 A1* | 3/2011 | Hua | G02B 27/017 359/464 |
| 2012/0105473 A1* | 5/2012 | Bar-Zeev | G06F 3/012 345/633 |
| 2012/0127062 A1* | 5/2012 | Bar-Zeev | G02B 3/14 345/6 |
| 2012/0127284 A1* | 5/2012 | Bar-Zeev | G02B 27/017 348/53 |

FOREIGN PATENT DOCUMENTS

| | | |
|---|---|---|
| EP | 2 341 388 A1 | 7/2011 |
| JP | 3342423 B2 | 11/2002 |
| JP | 2009003812 A | 1/2009 |
| JP | 2010134460 A | 6/2010 |
| JP | 4609581 B2 | 1/2011 |
| JP | 2012066002 A | 4/2012 |
| WO | 2010044383 A1 | 4/2010 |

OTHER PUBLICATIONS

May 21, 2013 International Preliminary Report on Patentability issued in International Application No. PCT/JP2013/061897.

Dec. 8, 2015 Extended Search Report issued in European Patent Application No. 13794149.8.

* cited by examiner (a)

(b)

a = LENS DATA FOR LEFT EYE
b = LENS DATA FOR RIGHT EYE
c = ORIGINAL IMAGE FOR LEFT EYE
d = ORIGINAL IMAGE FOR RIGHT EYE
e = DEPTH IMAGE FOR LEFT EYE
f = DEPTH IMAGE FOR RIGHT EYE
g = DISTORTION FOR LEFT EYE
h = DISTORTION FOR RIGHT EYE
i = PSF FOR LEFT EYE
j = PSF FOR RIGHT EYE
k = SIMULATION IMAGE FOR LEFT EYE
l = SIMULATION IMAGE FOR RIGHT EYE

SIMULATION DEVICE

TECHNICAL VISUAL FIELD

The present invention relates to a simulation device for virtually displaying an image to be viewed through a spectacle lens by a wearer of the spectacle lens.

DESCRIPTION OF RELATED ART

In recent years, for example in a spectacle shop, a simulation device is utilized, for virtually experiencing a wearing state of a spectacle lens by a prospective wearer of the spectacle lens (for example, see patent documents 1 and 2). By using such a simulation device, the prospective wearer of the spectacle lens can experience a view (distortion or blurring of an image) through the spectacle lens prior to ordering a lens. Also, at the spectacle shop side, since an image formation by simulation is used, there is no necessity for preparing a sample lens such as a lens prescription desired by the spectacle wearer, and the spectacle wearer can experience the view in the case of wearing a lens of the kind which is not found in the sample lens.

PRIOR ART DOCUMENT

Patent Document

Patent document 1: Patent Publication No. 3342423
Patent document 2: International Publication No. 2010/044383

SUMMARY OF THE INVENTION

Problem to be Solved by the Invention

Incidentally, in a conventional simulation device disclosed in patent document 1 or 2, etc., an original image (a still image or a movie) which is a base of an image formation by simulation, is limited to an image photographed in advance, or an image created by computer graphics (abbreviated as "CG" hereafter). Namely, the conventional simulation device is configured to make the spectacle lens wearer virtually experience a lens wearing state, using the original image prepared in advance.

The reason for using the original image prepared in advance by the conventional simulation device is as follows. Not only lens data such as a lens prescription, etc., but also data of a distance from a lens to a component of the original image (for example, each pixel) is essential for the image formation by simulation. This is because a lens focal length is a fixed value in each spectacle lens, and therefore if the distance to the component of the original image is different, the view of the component through the spectacle lens is also naturally different. In this point, if the original image is prepared in advance, the distance to the component in the original image can be specified in advance. For example, in the case of the image created by CG, each pixel can have distance data. For this reason, the original image prepared in advance is used in the conventional simulation device.

However, if the image is limited to scenes created by CG prepared in advance, the spectacle wearer using the simulation device virtually experience the lens wearing state while viewing a different image from an image that is realistic in real space, and therefore the spectacle wearer possibly has an uncomfortable feeling. Meanwhile, as described in patent document 1, by using a plurality of imaging cameras utilizing a charge coupled device (CCD) and a complementary metal oxide semiconductor sensor (CMOS), etc., the original image and the corresponding distance data can be acquired by using a stereo vision photographed by such a plurality of imaging cameras. However, in this case, there is a problem that the distance data regarding a low contrast surface cannot be acquired, thus easily affected by a lighting condition. Therefore, there is a limit in the image that can be simulated. Further, due to a great calculation load for acquiring the distance data, there is also a problem that it is not suitable for acquiring the distance data in real time.

Therefore, an object of the present invention is to provide a simulation device capable of providing a virtual experience of a lens wearing state while viewing an image that is realistic in real space by a prospective wearer of a spectacle lens, and even in this case, creating a simulation image on which a difference of a view corresponding to a difference of a distance is correctly reflected.

In order to achieve the above-described object, the present invention is provided, and inventors of the present invention examine a use of an image that is realistic in real space as an original image which is a base of an image formation by simulation. Regarding this point, use of an imaging camera is considered for example, for photographing an image that is realistic in real space. The image that is realistic in real space called here, is the image realizing a real time display of an object (object to be imaged) in a visual field, while dynamically responding to the visual field of the prospective wearer of a spectacle lens. However, as described above, there is a limit in the distance data that can be acquired even in the case of using a stereo vision by a plurality of imaging cameras, thus limiting the image that can be simulated. Therefore, only an imaging result obtained by the imaging cameras is not suitable for the simulation of the virtual experience of the lens wearing state.

When simply specifying a distance, a distance measurement device such as a generally widely used infrared sensor is considered to be used. However, the distance is required to be specified for each component (for example each pixel) of the original image. Therefore, it is not necessarily realistic to detect the data of the distance regarding each pixel by using a general distance measuring device, in consideration of an information processing capability of a common simulator.

Regarding this point, as a result of strenuous efforts by the inventors of the present invention, an unconventionally new idea is found as follows. In order to achieve a real time display of an object in the visual field while dynamically responding to the visual field of the prospected wearer in such a simulation use of making the prospected wearer of the spectacle lens have the virtual experience of the lens wearing state, a depth sensor used for a monitoring system or a game machine, etc., is used for the simulation device which requires analysis processing such as ray tracing, etc., of an optical system, to thereby acquire a depth image by this depth sensor, in the same view angle as an imaging result obtained by the imaging cameras.

The present invention is provided based on a new concept by the abovementioned inventors of the present invention.

According to a first aspect of the present invention, there is provided a simulation device for virtually displaying an image to be viewed through a spectacle lens by a wearer of a spectacle lens, including:

an imaging camera configured to perform imaging in a visual field of the wearer;

a depth sensor configured to acquire a depth image in the same view angle as an imaging result obtained by the imaging camera;

a data acquisition unit configured to acquire lens data of the spectacle lens;

an image creation unit configured to create a simulation image on which a view of an image to be viewed through the spectacle lens is reflected, by applying image processing to the imaging result obtained by the imaging camera, based on the depth image and the lens data; and an image displayer configured to display and output the simulation image as an image to be viewed through the spectacle lens.

According to a second aspect of the present invention, there is provided the simulation device of the first aspect, wherein at least the image creation unit and the image displayer are configured to individually respond to a simulation image for a left eye and a simulation image for a right eye respectively.

According to a third aspect of the present invention, there is provided the simulation device of the second aspect, wherein the imaging camera and the depth sensor are also individually provided, responding to the right and left eyes respectively.

According to a fourth aspect of the present invention, there is provided the simulation device of the first, second, or third aspect, wherein an image handled by the imaging camera, the depth sensor, the image creation unit, and the image displayer, is a movie.

According to a fifth aspect of the present invention, there is provided the simulation device of any one of the first to fourth aspects, wherein at least the imaging camera, the depth sensor, and the image displayer are assembled in a case that can be mounted on a head part of the wearer.

According to a sixth aspect of the present invention, there is provided the simulation device of the fifth aspect, wherein a camera driving mechanism is provided for changing an arrangement state of the imaging camera.

According to a seventh aspect of the present invention, there is provided the simulation device of any one of the first to fourth aspect, wherein at least the imaging camera, the depth sensor, and the image displayer are assembled in a portable information processing terminal machine.

Advantage of the Invention

According to the present invention, a simulation image can be created, which is capable of having a virtual experience of a lens wearing state while viewing an image that is realistic in real space by a prospected wearer of a spectacle lens, so that a difference of a view corresponding to a difference of a distance is correctly reflected on the simulation image.

MODES FOR CARRYING OUT THE INVENTION

An embodiment of the present invention is divided into a first embodiment and a second embodiment, which will be described hereafter sequentially, based on the drawings.

First Embodiment

The first embodiment is classified into the following items and explanation is given for each item respectively.
1. Schematic structure of a simulation device
2. Functional structure of the simulation device
3. Procedure of simulation processing
4. Effect of the first embodiment
5. Modified example, etc.

1. Schematic Structure of a Simulation Device

A schematic structure of the whole body of the simulation device according to the first embodiment will be described first.

Figure 1:
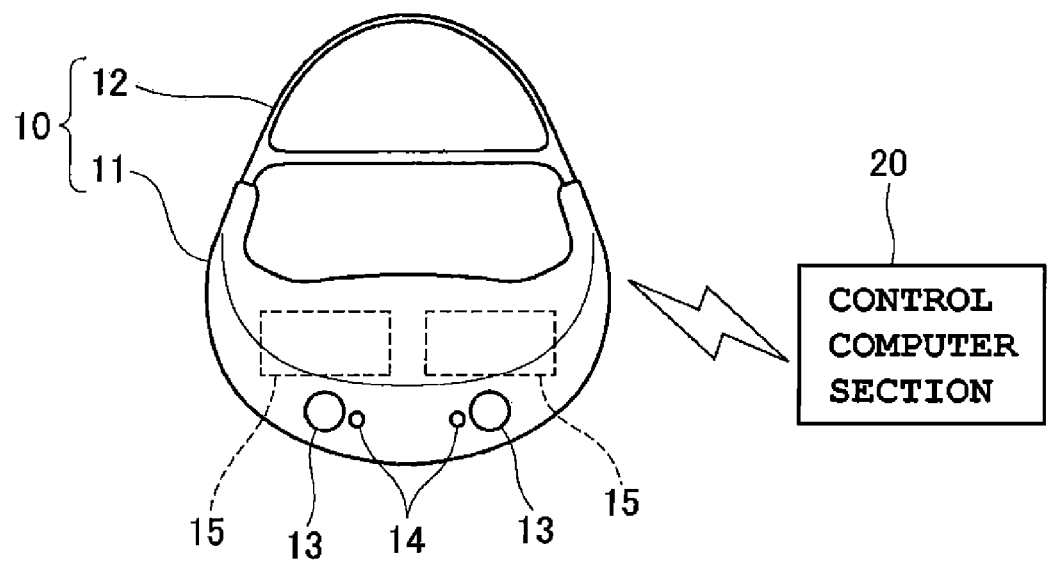
FIG. 1 is an explanatory view showing a schematic block diagram of the whole body of a simulation device according to a first embodiment of the present invention.
Figure 1:
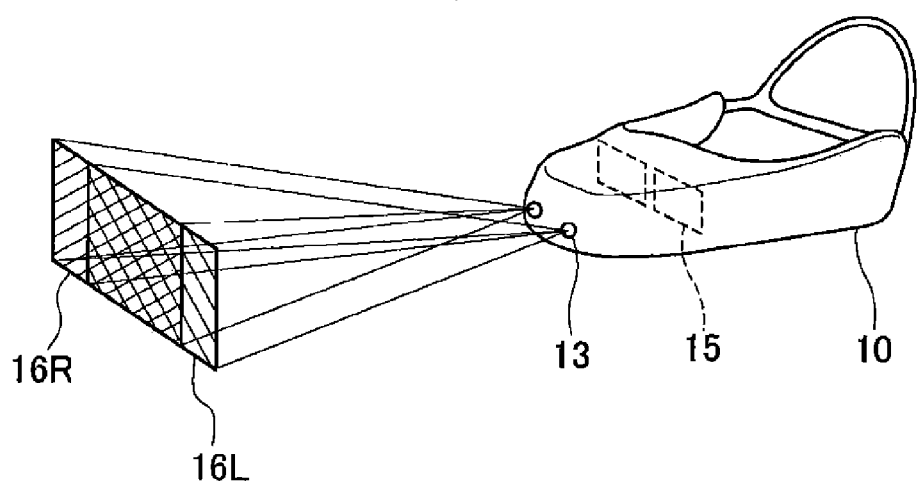

FIG. 1 is an explanatory view showing a schematic constitutional example of the whole body of the simulation device according to the first embodiment.

The simulation device of the first embodiment is configured to virtually display an image to be viewed through a spectacle lens by a wearer of the spectacle lens, thus giving a virtual experience of a lens wearing state to the prospected wearer of the spectacle lens. Therefore, as shown in FIG. 1(a), the simulation device of the first embodiment is configured so as to be roughly divided into a head mount display (abbreviated as "HMD" hereafter) section 10 and a control computer section 20.

(HMD Section)

The HMD section 10 includes a case 11 and a mount band 12 connected thereto, so as to be mounted on a head part of a prospected wearer of a spectacle lens (simply called a "lens wearer" hereafter). Then, imaging cameras 13, depth sensors 14, and image displayers 15 are assembled in the case 11.

The imaging camera 13 is configured to capture an image that is realistic in real space in which the lens wearer exists, by imaging an object (object to be imaged) that exists in a visual field of the lens wearer while dynamically responding to this visual field. The imaging camera 13 having a structure equipped with a CCD sensor and a CMOS sensor, is considered to be used. The imaging camera 13 is preferably provided individually so as to correspond to the right and left eyes of the lens wearer respectively. In this case, as shown in FIG. 1(b), one of the imaging cameras 13 provided individually performs imaging in an view angle 16L responding to the visual field of the left eye of the lens wearer, and the other imaging camera 13 performs imaging in an view angle 16R responding to the visual field of the right eye of the lens wearer. Preferably, the imaging camera 13 is also configured to respond to the imaging of a movie.

Each depth sensor 14 is configured to acquire a depth image in the same view angle as an imaging result obtained by each imaging camera 13. The "depth image" means the image having distance information from the depth sensor 14 to an object, instead of a color or a shade, etc., of a general two-dimensional RGB image. Namely, regarding the object in the image in the same view angle as the imaging result obtained by the imaging camera 13, it can be considered that the depth sensor 14 for acquiring a depth image, is configured to detect a size of a distance between the object and the depth sensor 14 in a depth direction of the view angle, for each pixel constituting the image of the object, with one frame being an assembly of the pixels as one unit. The distance may be detected using a publicly-known technique. TOF (Time Of Flight) system and SL (Structured Light) system, etc., can be given as a publicly-known technique for example, wherein the TOF system is the system of detecting the distance of the image by measuring a time required for an emitted light to return after it strikes the object, and the SL system is the system of measuring a distance by a distortion of a pattern of a reflected light after a laser beam having a specific pattern strikes the object.

Such a depth sensor 14 is preferably provided individually so as to respond to the right and left eyes of the lens wearer respectively, similarly to the imaging cameras 13. However, even in a case that the imaging cameras 13 are individually provided so as to respond to the right and left eyes of the lens wearer respectively, it can be considered that one depth sensor 14 is shared by the right and left eyes, if the depth sensor 14 has a function of correcting a distance detection result obtained by the depth sensor 14, for the right and left eyes.

Preferably, the depth sensor 14 can also respond to the movie similarly to the imaging camera 13, and if it can respond to a movie with a high frame rate, this is further preferable because it can respond to a smooth image.

The depth sensor 14 is configured to acquire a depth image in the same view angle as the imaging result obtained by the imaging camera 13. "The same view angle" called here includes not only a case that the view angle coincides with each other completely, but also a case that the view angle is aligned with each other so as to be the same, although not completely the same.

The depth sensor 14 is not necessarily required to be a separate body from the imaging camera 13. Namely, the depth sensor 14 may be constituted integrally with the imaging camera 13, by using a camera device capable of simultaneously acquiring the general two-dimensional RGB image and the depth image having the distance information.

The image displayer 15 is arranged in front of the eyes of the lens wearer wearing the case 11 of the HMD section 10, and configured to display an image for the lens wearer. The image displayer 15 equipped with LCD (Liquid Crystal Display) is considered to be used. As described in detail later, the simulation image being the image supposed to be viewed by the lens wearer through the spectacle lens, can be given as the image displayed and outputted by the image displayer 15. Preferably, the image displayer 15 is constituted of a display panel for a left eye and a display panel for a right eye so as to individually respond to a simulation image for a left eye and a simulation image for a right eye respectively. Also preferably, the image displayer 15 is configured to respond to display and output of a movie.

(Control Computer Section)

The control computer section 20 has a function of performing information processing as a computer device based on a specific program, and specifically constituted of a combination of CPU (Central Processing Unit), HDD (Hard Disk Drive), ROM (Read Only Memory), RAM (Random Access Memory), and an external interface (I/F), etc. The control computer section 20 may be assembled in the case 11 of the HMD section 10 or may be provided separately from the HMD section 10. When the control computer section 20 is provided separately from the HMD section 10, the control computer section 20 can communicate with the HMD section 10 via a wire or a wireless communication line.

2. Functional Structure of the Simulation Device

Next, explanation is given for a functional structure of the simulation device of the first embodiment.

Figure 2:
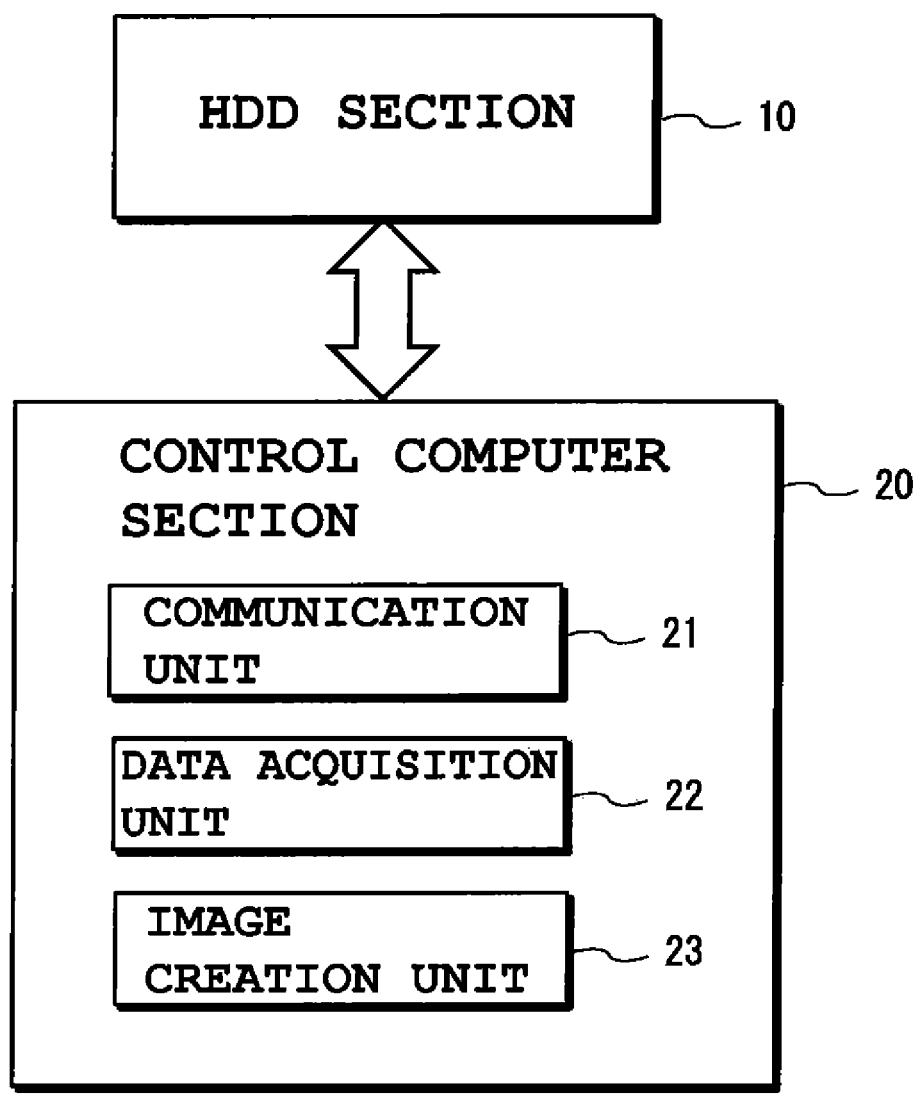
FIG. 2 is a block diagram showing a constitutional example of a function of the simulation device according to the first embodiment of the present invention.

FIG. 2 is a block diagram showing an example of the functional structure of the simulation device according to the first embodiment.

In the simulation device of the first embodiment, the function as a communication unit 21, a data acquisition unit 22, and an image creation unit 23, is realized by executing a specific program by the control computer section 20.

The communication unit 21 is a function for performing communication between the control computer section 20 and the HMD section 10. Specifically, the communication unit 21 receives an image captured by the imaging camera 13 and a depth image acquired by the depth sensor 14, or sends the simulation image created by the image creation unit 23 described later to the image displayer 15. A communication protocol used by the communication unit 21 is not particularly limited.

The data acquisition unit 22 is a function for acquiring lens data regarding the spectacle lens scheduled to be worn by the lens wearer. The acquired lens data includes at least lens prescription data and lens shape design data regarding the spectacle lens for a left eye and the spectacle lens for a right eye respectively. The lens prescription data is the data regarding a lens power, an addition power, a spherical power, an astigmatic power, an astigmatic axis, a prism power, a prism base direction, and a near inset amount, etc. The lens shape design data is the data regarding the shape of the spectacle lens, including a refractive index and Abbe number of a lens material, coordinate value data of a lens refractive surface (a front surface and a back surface), thickness data such as a lens central thickness, etc., data regarding a design parameter such as a corridor length, etc., and a refracting action (refractive power and a prism action, etc.) at each point on a lens. Such lens data may be acquired by accessing a data server device on a network line by the data acquisition unit 22 of the control computer section 20. The lens data can also be acquired by accessing a memory device by the data acquisition unit 22 of the control computer section 20, if the lens data is stored in a database in the memory device of the control computer section 20 for example. When there are various lens data regarding various spectacle lenses in the data server device, etc., for example, desired lens data may be acquired by searching the data, for example using a maker's name or product model numbers, etc., of the spectacle lens as a key, while following an operation instruction from an operating unit not shown of the HMD section 10 or the control computer section 20.

The image creation unit 23 has a function of creating the simulation image which is the image supposed to be viewed by the spectacle wearer through the spectacle lens. As described later in detail, the image creation unit 23 is configured to create the simulation image by performing image processing to the image captured by the imaging camera 13 and received by the communication unit 21 so that the view through the spectacle lens is reflected on the simulation image, based on the depth image acquired by the depth sensor 14 and received by the communication unit 21, and the lens data of the spectacle lens acquired by the data acquisition unit 22. Preferably the image creation unit 23 can create the simulation image for a left eye and the simulation image for a right eye, so as to individually respond to the simulation image for a left eye and the simulation image for a right eye respectively. Also preferably, the image creation unit 23 responds to the creation of the simulation image of a movie.

The abovementioned communication unit 21, data acquisition unit 22, and image creation unit 23 are realized by executing a specific program (namely a simulation executing program) by the control computer section 20 having the function as a computer device. In this case, the simulation executing program is used by being installed on the HDD, etc., of the control computer section 20. However, the simulation executing program may be provided through a network line connected to the control computer section 20, before it is installed thereon, or may be provided by being stored in a memory medium that can be read by the control computer section 20.

3. Procedure of the Simulation Processing

Next, in the simulation device thus configured, explanation will be given for a procedure of executing the simulation processing for making the lens wearer have the virtual experience of the wearing state of the spectacle lens.

Figure 3:
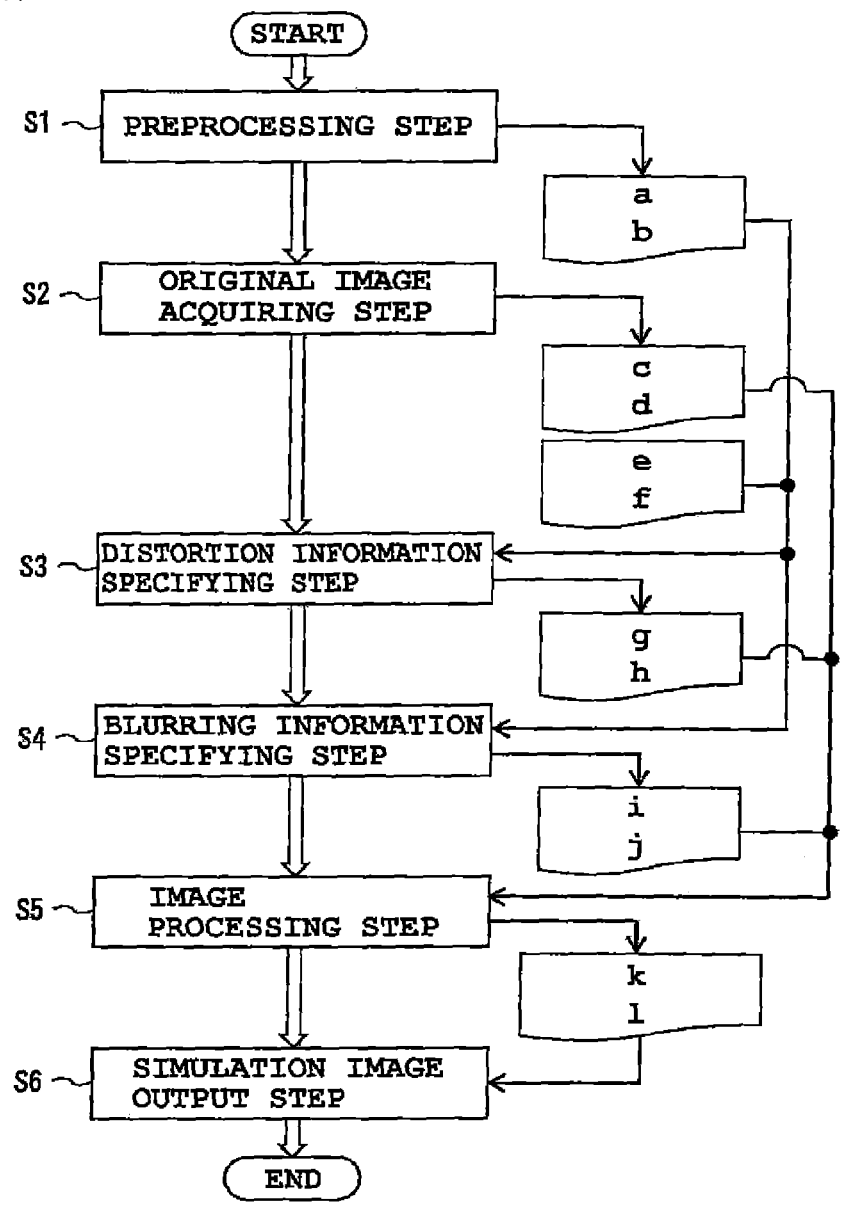
FIG. 3 is a flowchart showing an example of a procedure of executing a simulation processing performed by the simulation device according to the first embodiment of the present invention.

FIG. 3 is a flowchart showing an example of the procedure of executing the simulation processing performed by the simulation device of the first embodiment.

The simulation processing described in the first embodiment is roughly divided into a preprocessing step (S1), an original image acquiring step (S2), a distortion information specifying step (S3), a blurring information specifying step (S4), an image processing step (S5), and a simulation image output step (S6).

In the preprocessing step (S1), prior to a series of processing after the original image acquiring step (S2), lens data regarding a spectacle lens to be worn by a lens wearer, is acquired by the data acquisition unit 22. At this time, the data acquisition unit 22 is configured to acquire the lens data regarding a spectacle lens for a left eye and a spectacle lens for a right eye respectively. The lens wearer may specify the spectacle lens to be worn by following an operation instruction of an operation unit not shown of the HMD section 10 or the control computer section 20.

In the original image acquiring step (S2), an object (object to be imaged) that exists in a visual field of the lens wearer is imaged by the imaging cameras 13 built in the HMD section 10 in a state of mounting the HMD section 10 on a head part of the lens wearer. Then, a captured image obtained by the imaging cameras 13 is received by the communication unit 21, and the obtained captured image is defined as an original image which is a base of a simulation image. Thus, for example if the imaging cameras 13 are individually provided so as to respond to the right and left eyes of the lens wearer, an original image for a left eye corresponding to the visual field of the left eye of the lens wearer, and an original image for a right eye corresponding to the visual field of the right eye of this lens wearer, are respectively acquired by the control computer section 20.

Further, in the original image acquiring step (S2), a depth image in the same view angle as the imaging result is acquired by the depth sensor 14, and the acquired depth image is received by the communication unit 21. Thus, when the original image for a left eye and the original image for a right eye are acquired based on the imaging result obtained by the imaging cameras 13 for example by the control computer section 20, the control computer section 20 can grasp distance information (size of the distance) regarding each pixel constituting the original image for a left eye, and distance information (size of the distance) regarding each pixel constituting the original image for a right eye respectively. When the imaging cameras 13 can respond to imaging of a movie, the depth image is also acquired by the depth sensor 14 individually for each frame, because the movie is constituted of a plurality of continuous frames of still images.

In the distortion information specifying step (S3), a mode of the distortion of the image generated when viewing the object through the spectacle lens to be worn by the lens wearer, is specified by the image creation unit 23 for the spectacle lens for a left eye and the spectacle lens for a right eye respectively. When viewing the object through the spectacle lens, a light beam is refracted. Namely, a position of an object point when viewing the object with a naked eye, is moved to another position when viewing the object through the spectacle lens. The distortion of the image is generated by such a movement.

The generation mode of the distortion of the image can be specified by recognizing a position of an arbitrary light transmission point in the spectacle lens based on the lens data acquired in the preprocessing step (S1), and recognizing a size of the distance from the spectacle lens to the imaged object based on the depth image acquired in the original image acquiring step (S2), and using a technique of ray tracing. At this time, the depth image acquired by the depth sensor 14 is obtained by specifying a distance between the depth sensor 14 and the object to be imaged. However, the depth sensor 14 and the spectacle lens are provided at vicinity positions, and therefore the distance specified in the depth image by the depth sensor 14 may be virtually defined as the distance between the spectacle lens and the object to be imaged, or the distance between the spectacle lens and the object to be imaged may be calculated by correcting the depth image by carrying out a specific calculation processing, the depth image being obtained by the depth sensor 14. Thus, regarding the component (for example, each pixel) of the original image, the distance between the spectacle lens and the object to be imaged is known, and therefore the distortion of the image can be specified. Regarding the technique of ray tracing, a publicly-known technique may be used (see U.S. Pat. No. 3,342,423, International Publication No. 2010/044383), and therefore detailed explanation thereof is omitted.

Further, when specifying the distortion of the image, it can be considered that the processing load can be reduced by utilizing an approximation of light beam data by spline interpolation. Note that regarding the approximation of light beam data by spline interpolation as well, a publicly-known technique may be utilized. (see U.S. Pat. No. 3,342,423, International Publication No. 2010/044383).

In the blurring information specifying step (S4), the image creation unit 23 specifies a generation mode of image blurring generated when viewing the object through the spectacle lens to be worn by the lens wearer, regarding the spectacle lens for a left eye and the spectacle lens for a right eye. The image blurring is generated when viewing the object through the spectacle lens by the fact that all light beams from an object point are not converged to one point on retina. Namely, the light beams from the object point forms a light quantity distribution which is spread over a certain range, with an image point as a center. Such a distribution is called a point spread function (abbreviated as "PSF" hereafter). Accordingly, the generation mode of the image blurring can be specified by obtaining the PSF.

However, even when viewing the object through the same position on the spectacle lens, PSF is different if the distance to the object point is different. Meanwhile, in the image creation unit 23, the distance of the component (for example each pixel) of the original image is also known similarly to the case of the distortion information specifying step (S3) due to the depth image acquired in the original image acquiring step (S2), and therefore PSF which is different depending on the distance can be appropriately obtained. PSF may be obtained by using a publicly-known technique (see Patent Publication No. 3342423, International Publication No. 2010/044383), after recognizing the position of an arbitrary light transmission point in the spectacle lens based on the lens data acquired in the preprocessing step (S1), and recognizing the size of the distance to the object based on the depth image acquired in the original image acquiring step (S2).

In the image processing step (S5), the image creation unite 23 performs image processing to the original image for a left eye and the original image for a right eye respectively acquired in the original image acquiring step (S2), so that the view through the spectacle lens is reflected on the original images. Specifically, image processing is performed to the original image for a left eye, so that the distortion specified in the information specifying step (S3) and the blurring specified by PSF obtained in the blurring information specifying step (S4) are reflected on the original image for a left eye. Then, the image obtained by the image processing is used as the simulation image for a left eye. Also, image processing is performed to the original image for a right eye, so that the distortion specified in the information specifying step (S3) and the blurring specified by PSF obtained in the blurring information specifying step (S4) are reflected on the original image for a right eye. Then, the image obtained by the image processing is used as the simulation image for a right eye.

The image processing in the image processing step (S5) is considered to be performed as follows for example.

The distortion can be reflected by obtaining a correlation between the image side and the object side regarding all pixels in the visual field, and applying (moving) brightness information of the original image based on the correlation. Thus, image distortion in which the distortion information is reflected on the original image, can be obtained.

Blurring can be reflected on the original image by distributing brightness of each pixel to circumferential pixels based on the PSF, and reconstructing the brightness of all pixels of the image. Such a processing is called a convolution.

Namely, in the image processing step (S5), by performing convolution operation of the image distortion and PSF of each pixel, the simulation image is created from the original image.

Regarding a detailed technique, etc., of the image processing performed in the image processing step (S5), a publicly-known technique may be used (see U.S. Pat. No. 3,342,423, International Publication No. 2010/044383), and therefore explanation thereof is omitted here.

In the simulation image output step (S6), the simulation image for a left eye and the simulation image for a right eye created in the image processing step (S5) are respectively sent to the image displayer 15 by the communication unit 21. Thus, in the image displayer 15, the simulation image for a left eye is displayed and outputted in a display panel portion for a left eye, and the simulation image for a right eye is displayed and outputted in a display panel portion for a right eye respectively.

In the case of a movie for example, such a series of simulation processing is repeatedly performed by the simulation device, for each frame constituting the movie.

If the above-described simulation processing is performed, the lens wearer with the HMD section 10 mounted on the head part, can have the virtual experience of the wearing state of the spectacle lens, by viewing the simulation image on which the view through the spectacle lens is reflected.

4. Effect of the First Embodiment

According to the simulation device described in the first embodiment, the following effect can be obtained.

The simulation device of the first embodiment includes the imaging cameras 13, and the imaging result obtained by the imaging cameras 13 is used as the original image which is the base of the simulation image. Accordingly, when the spectacle wearer has the virtual experience of the wearing state of the spectacle lens, not the image of a virtual space drawn by CG, but the image that is realistic in real space where the lens wearer exists, can be displayed in real time, while dynamically responding to the visual field of the lens wearer.

In addition, even in this case, distance information (size of the distance) can be grasped regarding each pixel constituting the original image based on the depth image, and the difference of view corresponding to the difference of distance can be correctly reflected on the original image. Namely, by using the depth image acquired by the depth sensor 14, distance information regarding each pixel constituting a frame, with one framed as one unit, can be collectively obtained, unlike a case of detecting distance data regarding each pixel individually for each pixel, by using a general distance measurement device. Therefore, excessive processing load can be prevented at the time of the simulation processing, and the simulation device of the first embodiment is extremely suitable for the real time display of the simulation image.

As described above, according to the first embodiment, the simulation device is provided which is capable of providing the virtual experience of the lens wearing state while viewing the image that is realistic in real space by a prospective wearer of the spectacle lens, and even in this case, creating a simulation image on which the difference of a view corresponding to the difference of a distance is correctly reflected.

Further, the simulation device of the first embodiment is configured so that the lens data acquired by the data acquisition unit 22 and displayed in the image displayer 15, and the simulation image created by the image creation unit 23, individually respond to right and left eyes of the lens wearer respectively. Therefore, the simulation image which is different between right and left eyes can be displayed and outputted. Thus, according to the simulation device of the first embodiment, even in the case of a prescription of the spectacle lens different between right and left eyes, the simulation image can be displayed and outputted for the lens wearer so that the view through each spectacle lens is correctly reflected on the simulation image. Further, if each simulation image responding to right and left eyes is used in consideration of a convergence angle of the right and left eyes, the simulation device can also respond to a stereoscopic image called 3D.

The simulation device of the first embodiment can also individually respond to the right and left eyes of the lens wearer, for not only the image displayer 15, the lens data, and the simulation image, but also the imaging cameras 13 and the depth sensors 14 in the HMD section 10. Accordingly, even when the simulation device different between right and left eyes of the lens wearer is displayed and outputted as described above, the original image obtained by the imaging cameras 13 and the depth image obtained by the depth sensors 14 can be used as they are. Namely, for example there is no necessity for performing complicated processing such as applying data correction processing to one original image for example and obtaining the original image for a left eye and the original image for a right eye, and therefore processing load can be reduced in the simulation processing, compared with a case that the complicated processing is necessary.

The simulation device of the first embodiment is configured to respond to the movie which is the image handled by the imaging cameras 13, the depth sensors 14, the image creation unit 23, and the image displayer 15, and therefore the lens wearer viewing the simulation image easily has a real time feeling or a sense of realism, and therefore the simulation device of the first embodiment is extremely suitable for having the virtual experience of the wearing state of the spectacle lens by the lens wearer. Specifically, for example when the direction of the head part is changed by the lens wearer with the HMD section 10 mounted thereon, the simulation image corresponding to the visual field before change of the direction of the head part, is continued to be displayed and outputted in the case of the still image. However, if the simulation device can respond to the movie, display/output content of the simulation image can be switched responding to the change of the direction of the head part by the lens wearer.

Further, the simulation device of the first embodiment is configured so that at least the imaging cameras 13, the depth sensors 14, and the image displayer 15 are assembled in the case 11 of the HMD section 10. Accordingly, if the HMD section 10 is mounted on the head part, the lens wearer can view the object (imaged object) that exists in the visual field in a direction in which the head part is directed, as the simulation image on which the view through the spectacle lens is correctly reflected. Namely, according to the simulation device of the first embodiment, the HMD section 10 may be simply mounted on the head part by the lens wearer for having the virtual experience of the wearing state of the spectacle lens, and therefore the simulation device of the first embodiment has an excellent user-friendliness.

5. Modified Example, Etc.

The first embodiment is described above. However, the above-described disclosure content simply shows exemplary embodiment of the present invention, and the technical range of the present invention is not limited to the above-mentioned exemplary embodiment.

Modified examples of the abovementioned embodiment will be described hereafter.

In the abovementioned first embodiment, examples are given for a case that the imaging cameras 13 and the depth sensors 14, etc., are individually provided responding to the right and left eyes of the lens wearer respectively. However, it is also acceptable that one imaging camera and one image sensor, etc., are shared by right and left eyes.

For example, even in a case that one imaging camera 13 is shared by right and left eyes, the original image for a left eye and the original image for a right eye can be obtained by performing data correction processing to one original image based on the distance information specified from the depth image, if the depth image is acquired for the right and left eyes respectively. Specifically, the original image for a left eye and the original image for a right eye viewed from a view point of each of the right and left eyes, can be created from the image photographed by one imaging camera 13 arranged at an intermediate position between the right and left eyes and the depth image thereof. In this case, the original image for a left eye and the original image for a right eye are created from one original image, and therefore there is a merit that alignment adjustment of the imaging results by each imaging camera 13 is not required, unlike the case of using a plurality of imaging cameras 13.

Further, for example, it can be considered that one depth sensor 14 arranged in the intermediate position between right and left eyes is shared, because the distance to the object is not largely different between right and left eyes.

Further, in the abovementioned first embodiment, examples is given for a case that the imaging camera 13 is fixed to a position where the image in the view angle corresponding to the visual field of the lens wearer can be imaged by the imaging camera 13. However, the imaging camera 13 may be movably supported by a mechanism including a driving source such as a motor, etc.

In this case, for example, by moving the positions of the imaging cameras 13 provided individually responding to the right and left eyes of the lens wearer respectively, an interval between the imaging cameras 13 can be matched with a pupillary distance (PD) of the lens wearer.

Further, for example, in the case of a near vision by the lens wearer, the view angle in which the image is captured, can be set in an inset state by turning the imaging camera 13.

Second Embodiment

A second embodiment of the present invention will be described next. Note that different points from the abovementioned embodiment will be mainly described here.

The second embodiment is classified into the following items and explanation is given for each item respectively.
6. Schematic structure of the simulation device
7. Functional structure of the simulation device
8. Procedure of the simulation processing
9. Effect of the second embodiment
10. Modified example, etc.

6. Schematic Structure of the Simulation Device

The schematic structure of the whole body of the simulation device according to the second embodiment will be described first.

Figure 4:
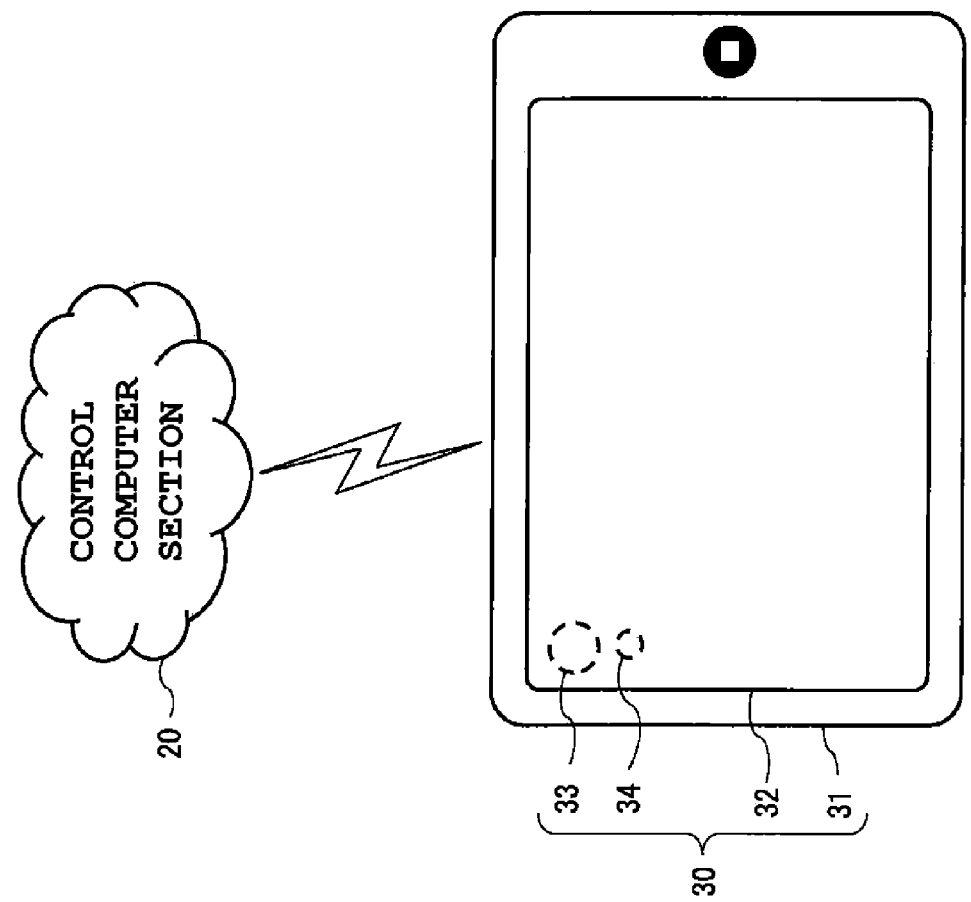
FIG. 4 is an explanatory view showing a schematic constitutional example of the whole body of a simulation device according to a second embodiment of the present invention.

FIG. 4 is an explanatory view showing the schematic structure of the whole body of the simulation device according to the second embodiment.

The simulation device of the second embodiment is roughly divided into an information processing terminal section 30 and a control computer section 20. Namely, the simulation device of the second embodiment includes the information processing terminal section 30 instead of the HMD section 10 described in the first embodiment.

(Information Processing Terminal Section)

The information processing terminal section 30 is constituted of a portable information processing terminal machine such as a tablet terminal, a smartphone, or PDA (Personal Digital Assistants), etc., for example, and is configured so that the lens wearer can use it in hand. Therefore, the information processing terminal section 30 includes a plate-shaped (tablet-shaped) case 31 having a size that can be grasped in hand by the lens wearer. Then, an image displayer 32 is assembled in one of the surfaces (the surface on the side that is visible to the lens wearer), and the imaging cameras 33 and the depth sensors 34 are assembled in the other surface (the surface on the side not visible by the lens wearer). The image displayer 32 has a function of inputting information, etc., as a touch panel by operating it by the lens wearer. Also, a function of processing information indicated by a specific program as a computer device is assembled in the case 31 (not shown). The information processing terminal section 30 is configured to carry out information communication, etc., with outside by these functions.

Similarly to the image displayer 15 described in the first embodiment, the image displayer 32 displays an image to the lens wearer. However, unlike the case of the first embodiment, only one image displayer 32 is assembled in the case 31, for selectively displaying either one of the simulation image for a left eye and the simulation image for a right eye. Note that the image displayer 32 is not necessarily limited to one, and may be constituted of a display panel for a left eye and a display panel for a right eye similarly to the case of the first embodiment. It is also acceptable that an area of one display screen is divided so as to respond to the simulation image for a left eye and the simulation image for a right eye respectively.

The imaging camera 33 is configured to capture an image that is realistic in real space where the lens wearer exists, similarly to the imaging camera 13 described in the first embodiment. However, unlike the case of the first embodiment, only one image displayer 33 is assembled in the case 31, for selectively capturing the image in either one of the image angles responding to the visual field for a left eye and the visual field for a right eye of the lens wearer. Note that the image displayer 32 is not necessarily limited to one, and may be constituted of a display panel for a left eye and a display panel for a right eye similarly to the case of the first embodiment.

Similarly to the depth sensor 14 described in the first embodiment, the depth sensor 34 is configured to acquire the depth image in the same view angle as the imaging result obtained by the imaging camera 33. Similarly to the imaging cameras 33, in the depth sensor 34 as well, only one depth sensor 34 is assembled in the case 31. Note that when the imaging camera 33 is individually provided responding to the right and left eyes respectively, the depth sensor 34 is also preferably provided individually responding to the right and left eyes respectively.

Further, these imaging camera 33 and depth sensor 34 are preferably not configured as a separate body but configured integrally. Namely, the imaging camera 33 and the depth sensor 34 are preferably constituted of a monocular camera (sensor). This is because in the case of the monocular camera, miniaturization and a light weight of the information processing terminal section 30 can be easily achieved, compared with the case of a multiple eye.

Therefore, CMOS sensor that can simultaneously acquire a normal RGB image and the depth image having distance information, is considered to be used as the imaging camera 33 and the depth sensor 34. The CMOS sensor is constituted of integrated pixels (pixel Z) and RGB pixels for acquiring the depth image. According to this structure, the RGB image and the depth image can be simultaneously acquired by a single CMOS sensor (for example, see URL: http://www.nikkei.com/article/DGXNASFK24036_USA220CZ000000/).

In addition, it is conceivable to use an image sensor for a monocular 3D camera capable of 3D imaging by one image sensor for example, as the imaging camera 33 and the depth sensor 34. The image sensor allows one image sensor to simultaneously obtain the images for a left eye and right eye, by alternately arranging pixels for a left eye and a right eye, so that the light beams incident form right and left directions are converted to right and left electric signals respectively. According to this structure, three-dimensional information can be extracted by utilizing an image deviation of the left eye and the right eye, and further the depth image can be extracted from this three-dimensional information, and therefore the RGB image and the depth image can be simultaneously acquired by a single image sensor (for example, see UTL: http://panasonic.co.jp/news/topics/2013/108643.html).

(Control Computer Section)

The control computer section 20 has a function of processing information indicated by a specific program as a computer device, similarly to the case of the first embodiment. The control computer section 20 may be assembled in the case 31 of the information processing terminal section 30, namely may utilize the function as the computer device in this case 31. However, the control computer section 20 is preferably provided as a separate body from the information processing terminal section 30, if an information processing ability is taken into consideration. In this case, the control computer section 20 can carry out communication with the information processing terminal section 30 via a wire or wireless communication line (for example public wireless LAN). Namely, the control computer section 20 is provided for realizing a so-called cloud computing in terms of the information processing terminal section 30.

7. Functional Structure of the Simulation Device

In the simulation device of the second embodiment, the control computer section 20 has a function as the communication unit 21, the data acquisition unit 22, and the image creation unit 23. Each of the functions 21 to 23 is similar to the case of the first embodiment, and therefore explanation thereof is omitted here.

8. Procedure of the Simulation Processing

Next, in the simulation device of the second embodiment, explanation is given for a procedure of executing simulation processing performed for having the virtual experience of the wearing state of the spectacle lens by the lens wearer. Here, explanation is given, in a case that only one imaging camera 33 and depth sensor 34 are assembled in the information processing terminal section 30 as an example.

As shown in FIG. 3, the simulation processing described in the second embodiment includes: a preprocessing step (S1); an original image acquiring step (S2); a distortion information specifying step (S3); a blurring information specifying step (S4); an image processing step (S5); and a simulation image output step (S6). This point is similar to the case of the first embodiment, but is different from the case of the first embodiment in the following point.

In the preprocessing step (S1), the lens wearer operates the information processing terminal section 30, accesses the control computer section 20, and indicates from the information processing terminal section 30, which of the right and left eyes is selected to be processed. Under such indicated information, the control computer section 20 acquires the lens data regarding either one of the spectacle lens for a left eye and the spectacle lens for a right eye, by the data acquisition unit 22.

In the original image acquiring step (S2), the image of the object is captured by the imaging camera 33 assembled in the information processing terminal section 30, in a state that the information processing terminal section 30 is held in hand by the lens wearer, and the depth image in the same view angle as the imaging result is acquired by the depth sensor 34, and the captured image and the depth image are sent to the control computer section 20. Then, the control computer section 20 receives the captured image by the communication unit 21 and uses it as the original image which is the base of the simulation image, and also receives the depth image by the communication unit 21, and grasps the distance information (size of the distance) regarding each pixel constituting the captured image.

The distortion information specifying step (S3), the blurring information specifying step (S4), and the image processing step (S5) performed thereafter are similar to the case of the first embodiment. Thus, the control computer section 20 creates the simulation image corresponding to the imaging result obtained by the information processing terminal section 30.

In the simulation image output step (S6), the simulation image created in the image processing step (S5) is sent to the information processing terminal section 30 by the communication unit 21. Thus, in the information processing terminal section 30, the simulation image is displayed to the lens wearer by the image displayer 32.

Thereafter, when indicated contents are switched by the information processing terminal section 30 and either one of the left eye and the right eye to be processed is selected, the information processing terminal section 30 and the control computer section 20 performs repeatedly the abovementioned series of processing steps for the indicated contents after switch.

When the above-described simulation processing is performed, the lens wearer who operates the information processing terminal section 30 can have the virtual experience of the wearing state of the spectacle lens by viewing the simulation image on which the view through the spectacle lens is reflected.

9. Effect of the Second Embodiment

According to the simulation device described in the second embodiment, the following effect can be obtained.

According to the simulation device of the second embodiment, the lens wearer can have the virtual experience of the lens wearing state while viewing the image that is realistic in real space, and even in this case the simulation image can be created so that a difference of a view corresponding to a difference of a distance is correctly reflected on the simulation image. Namely, in the second embodiment as well, the effect similar to the case of the first embodiment can be obtained.

Further, the simulation device of the second embodiment is constituted including the information processing terminal section 30 instead of the HMD section 10 described in the first embodiment. Then, at least the image displayer 32, the imaging cameras 33, and the depth sensors 34 are assembled in the case 31 constituting the information processing terminal section 30. Further, the information processing terminal section 30 can carry out communication with the control computer section 20 that realizes cloud computing. Therefore, according to the simulation device of the second embodiment, the lens wearer can have the virtual experience of the wearing state of the spectacle lens by accessing the control computer section 20 from the information processing terminal section 30. Namely, the lens wearer can easily have the virtual experience of the wearing state of the spectacle lens using the information processing terminal section 30 possessed by this lens wearer for example, and such a simulation device is extremely excellent in usability. Further, the information processing terminal section 30 possessed by the lens wearer can be used at the side where a virtual experience service of the lens wearing state is provided to the lens wearer (such as a spectacle shop or a spectacle lens maker, etc.), and therefore a service at a low cost can be provided without requiring a special terminal device, etc.

Further, in the simulation device of the second embodiment, the simulation image is displayed on the image displayer 32 of the information processing terminal section 30. Therefore, unlike the case of the HMD section 10 described in the first embodiment, the simulation image can be viewed by plurality of persons at the same time. Therefore, according to the simulation device of the second embodiment, for example, an interactive virtual experience service of the lens wearing state can be constructed in such a manner that the characteristic of the simulation image is shown to the lens wearer by stuff of the spectacle shop while viewing the simulation image at the same time by the lens wearer and the stuff of the spectacle shop.

10. Modified Example, Etc.

The second embodiment of the present invention is described above. However, the abovementioned disclosed content simply shows exemplary embodiments of the present invention, and a technical range of the present invention is not limited to the abovementioned exemplary embodiments.

Modified examples other than the abovementioned embodiments will be described hereafter.

In the abovementioned second embodiment, the simulation image displayed on the image displayer 32 of the information processing terminal section 30 is assumed to be the image corresponding to a total visual field of the lens wearer. The "total visual field" here means a viewing angle through the spectacle lens visible by the lens wearer, and for example means the range of about 90° in a horizontal direction and about 70° in a vertical direction.

Preferably, the information processing terminal section 30 has excellent portability or mobility. Therefore, it is probable that the image displayer 32 of the information processing terminal section 30 does not necessarily have a sufficient screen size for displaying the image corresponding to the total visual field of the lens wearer.

Therefore, the image displayer 32 of the information processing terminal section 30 may selectively display a partial visual field corresponding to the total visual field of the simulation image.

Figure 5:
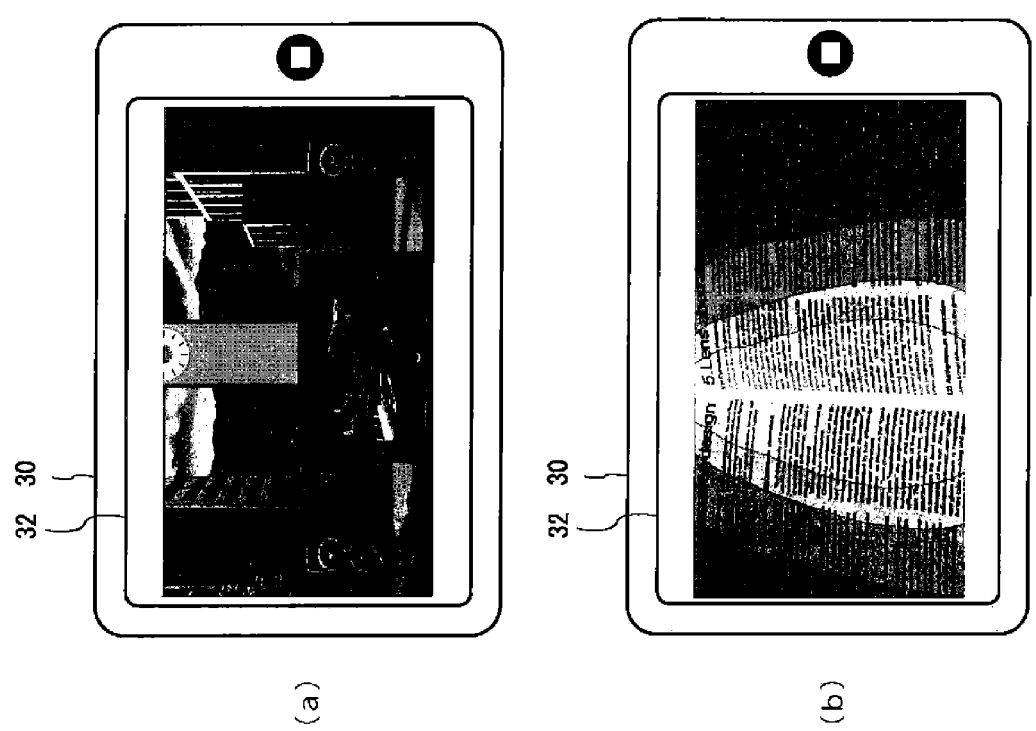
FIG. 5 is an explanatory view showing a display example of a simulation image obtained by the simulation device of the second embodiment of the present invention.

FIG. 5 is an explanatory view showing an example of displaying the simulation image by the simulation device of the second embodiment.

FIG. 5(*a*) shows an example of a state in which a partial area including a central portion out of a right side portion, a central portion, and a left side portion in a distance vision area, is displayed on the image displayer 32 as a partial visual field corresponding to a part of the total visual field, when the spectacle lens is a progressive addition lens.

Also, FIG. 5(b) shows an example of a state in which a partial area including a central portion out of a right side portion, a central portion, and a left side portion in a near vision area, is displayed on the image displayer 32 as a partial visual field corresponding to a part of the total visual field, when the spectacle lens is a progressive addition lens.

As represented by these display examples, when the spectacle lens is a progressive addition lens, it can be considered that for example a total visual field area is divided into nine areas in the image displayer 32, and any one of the right side portion, the central portion, and the left side portion in the distance vision area, and the right side portion, the central portion, and the left side portion in the near vision area, and the right side portion, the central portion, and the left side portion in the intermediate vision area, is selectively displayed in a state that each portion belongs to a different area. The plurality of partial visual field areas may correspond to a portion of the total visual field area respectively, and each partial visual field area may have a mutually overlapped image portion.

Such a selective display of the partial visual field can be realized by dividing the original image acquired in the original image acquiring step (S2) based on a specific dividing mode, and performing image processing of the image processing step (S5) in each area. Further, when performing the selective display of each partial visual field, it is conceivable to use a publicly-known function of the information processing terminal section 30, for switching a display (switching of a partial visual field) on the image displayer 32.

As described above, in the case of the selective display of each partial visual field, the image can be displayed and outputted without requiring reduction, etc., of the simulation image even in the case that the image displayer 32 does not have a sufficient screen size. In addition, even in the case of the selective display of each partial visual field, the lens wearer, etc., can recognize the total visual field through switching of the display. Namely, the selective display of each partial visual field given here for example, is extremely suitable when it is applied to the image displayer 32 that does not have a sufficient screen size, and compatibility with the information processing terminal section 30 would be extremely high, because mobility or portability is very important.

Further, as shown in FIG. 5(a) and FIG. 5(b), the simulation image displayed on the image displayer 32 of the information processing terminal section 30 may be a superimposition of articulation index contour images. The "articulation index" is one of the indexes for evaluating a performance of the spectacle lens (particularly progressive addition lens). Explanation for details of the articulation index is omitted here, because it is based on a publicly-known technique (for example, see U.S. Pat. No. 3,919,097).

The superimposition of the articulation index contour images can be realized by obtaining the articulation index of the spectacle lens based on the lens data acquired in the preprocessing step (S1), and creating the image showing the contour of the articulation index, and synthesizing the contour image with the simulation image.

By performing such a superimposition of the articulation index contour images, the lens visual characteristic can be easily grasped, compared with a case without superimposition of the contour images. This is effective for a case that a resolution of the image displayer 32 is not sufficient. This is because when the resolution of the image displayer 32 is not sufficient, there is a possibility that the blurring and the distortion, etc., reflected on the simulation image, cannot be completely reproduced, but if the contour images are superimposed, such a portion that cannot be completely reproduced can be complemented by contours. If the image displayer 32 may have a low resolution, the lens wearer can have the virtual experience of the lens wearing state using a small, light weight, and inexpensive information processing terminal section 30. Further, if the contour images are superimposed, subtle differences of the lens visual characteristics of each spectacle lens becomes apparent by a difference of the superimposed contour images.

DESCRIPTION OF SIGNS AND NUMERALS

10 HMD section
13 Imaging camera
14 Depth sensor
15 Image displayer
20 Control computer section
21 Communication unit
22 Data acquisition unit
23 Image creation unit
30 Information processing terminal section
32 Image displayer
33 Imaging camera
34 Depth sensor

The invention claimed is:

1. A simulation device for displaying a simulation image of a view through a spectacle lens by a wearer of the spectacle lens, comprising:
    an imaging camera configured to perform imaging in a visual field of the wearer and obtain an imaging result of the view;
    a depth sensor configured to acquire a depth image in the same view angle as the imaging result obtained by the imaging camera;
    a data acquisition computer device configured to acquire lens data of the spectacle lens by accessing a memory device in which the lens data is stored, the lens data including at least prescription data and lens shape design data;
    a distortion generation mode specification computer device configured to specify a generation mode of a distortion in the view through the spectacle lens based on the depth image and the lens data;
    a distortion image generation computer device configured to generate a distortion image in which the distortion is reflected on the imaging result based on the generation mode of the distortion;
    a blurring generation mode specification computer device configured to specify a generation mode of a blurring in the view through the spectacle lens by obtaining a point spread function in the view through the spectacle lens based on the depth image and the lens data;
    an image creation computer device configured to create a simulation image in which the distortion and the blurring are reflected on the imaging result by performing a convolution operation of the distortion image and the point spread function; and
    an image displayer configured to display and output the simulation image.

2. The simulation device according to claim 1, wherein at least the distortion generation mode specification computer device, the distortion image generation computer device, a blurring generation mode specification computer device, the image creation computer device and the image displayer are configured to individually respond to a simulation image for a left eye and a simulation image for a right eye respectively.

3. The simulation device according to claim 2, wherein the imaging camera and the depth sensor are also individually provided, responding to the right and left eyes respectively.

4. The simulation device according to claim 1, wherein an image handled by the imaging camera, the depth sensor, the distortion generation mode specification computer device, the distortion image generation computer device, a blurring generation mode specification computer device, the image creation computer device, and the image displayer, is a movie.

5. The simulation device according to claim 1, wherein at least the imaging camera, the depth sensor, and the image displayer are assembled in a case that can be mounted on a head part of the wearer.

6. The simulation device according to claim 5, wherein a camera driving mechanism is provided for changing an arrangement state of the imaging camera.

7. The simulation device according to claim 1, wherein at least the imaging camera, the depth sensor, and the image displayer are assembled in a portable information processing terminal machine.

* * * * *